US008685947B2

(12) United States Patent
Mathiowitz et al.

(10) Patent No.: US 8,685,947 B2
(45) Date of Patent: Apr. 1, 2014

(54) COMPOSITIONS AND METHODS FOR LOOP DIURETICS WITH CONSISTENT BIOAVAILABILITY

(75) Inventors: Edith Mathiowitz, Brookline, MA (US); Bryan Laulicht, Great Neck, NY (US)

(73) Assignee: Brown University, Providence, RI (US)

( * ) Notice: Subject to any disclaimer, the term of this patent is extended or adjusted under 35 U.S.C. 154(b) by 33 days.

(21) Appl. No.: 13/217,764

(22) Filed: Aug. 25, 2011

(65) Prior Publication Data

US 2012/0053156 A1 Mar. 1, 2012

Related U.S. Application Data

(60) Provisional application No. 61/376,737, filed on Aug. 25, 2010.

(51) Int. Cl.
| | | |
|---|---|---|
| *A01N 51/00* | (2006.01) | |
| *A61K 31/655* | (2006.01) | |
| *A61K 47/32* | (2006.01) | |
| *B32B 5/16* | (2006.01) | |
| *B32B 9/00* | (2006.01) | |
| *B32B 15/02* | (2006.01) | |
| *B32B 17/02* | (2006.01) | |
| *B32B 19/00* | (2006.01) | |
| *B32B 21/02* | (2006.01) | |
| *B32B 23/02* | (2006.01) | |
| *B32B 27/02* | (2006.01) | |
| *C07D 307/02* | (2006.01) | |

(52) U.S. Cl.
USPC ............................. 514/158; 428/402; 549/494

(58) Field of Classification Search
None
See application file for complete search history.

(56) References Cited

U.S. PATENT DOCUMENTS

2006/0057197 A1* 3/2006 Han et al. ...................... 424/468
2007/0281007 A1* 12/2007 Jacob et al. .................... 424/452
2009/0011019 A1* 1/2009 Jahagirdar et al. ............ 424/472

OTHER PUBLICATIONS

Lee et al. (ACTA Paediatr Sin, Zhonghua Min Guo Xiao Er Ke Yi Xue Zai Zhi May-Jun. 1994 35 (3) 215-220).*
Aceves et al. "Preparation and characterization of Furosemide-Eudragit controlled release systems" Intl J Pharm, 2000, vol. 195, pp. 45-53.
Bardonnet et al. "Gastroretentive dosage forms: Overview and special case of Helicobacter pylori" J Control Release, 2006, vol. 111, pp. 1-18.
Beyers et al. "Structure-Solubility Relationship and Thermal Decomposition of Furosemide" Drug Develop Industrial Pharm, 2000, vol. 26, pp. 1077-1083.
Carino et al. "Nanosphere based oral insulin delivery" J Control Release, 2000, vol. 65, pp. 261-269.
Cilurzo et al. "Polymethacrylate salts as new low-swellable mucoadhesive materials" J Control Release, 2003, vol. 88, pp. 43-53.
Davis et al. "Formulation strategies for absorption windows" Drug Disc Today, 2005, vol. 10, pp. 249-257.
Di Colo et al. "In vitro evaluation of a system for pH-controlled peroral delivery of metformin" J Control Release, 2002, vol. 80, pp. 119-128.
Dormans et al. "Diuretic Efficacy of High Dose Furosemide in Severe Heart Failure: Bolus Injection Versus Continuous Infusion" J Am Coll Cardiol, 1996, vol. 28, pp. 376-382.
Gimenez et al. "Molecular mechanisms and regulation of furosemide-sensitive Na-K-Cl cotransporters" Curr Op Nephrol Hyperten, 2006, vol. 15, pp. 517-523.
Gohary et al. "Release of furosemide from sustained release microcapsules prepared by phase separation technique" Drug Develop Industrial Pharm, 1991, vol. 17, pp. 443-450.
Hammarlund et al. "Acute tolerance to furosemide diuresis in humans. Pharmacokinetic-Pharmacodynamic Modeling" J Pharm Exp Thera, 1985, vol. 233, pp. 447-453.
Kislalioglu et al. Physical characteristics and dissolution properties of ibuprofen: eudragit coprecipitates, J Pharm Sci, 1991, vol. 80, pp. 799-804.
Laulicht et al. "Are in vivo gastric bioadhesive forces accurately reflected by in vitro experiments?" J Control Release, 2009, vol. 134, pp. 103-110.
Laulicht et al. "Diuretic bioactivity optimization of furosemide in rats" Eur J Pharm Biopharm, 2011, vol. 79, pp. 314-319.
Moustafine et al. "Characteristics of interpolyelectrolyte complexes of Eudragit E100 with Eudragit L100" J Control Release, 2005, vol. 103, pp. 191-198.
Murray et al. "Variable furosemide absorption and poor predictability of response in elderly patients" Pharmacotherapy, 1997, vol. 17, pp. 98-106.
Ozdemir et al. "Studies of Floating Dosage Forms of Furosemide: In Vitro and In Vivo Evaluations of Bilayer Tablet Formulations Nurten" Drug Develop Industr Pharm, 2000, vol. 26, pp. 857-866.
Sakkinen et al. "Evaluation of microcrystalline chitosans for gastroretentive drug delivery" Eur J Pharm Sci, 2003, vol. 19, pp. 345-353.
Sakkinen et al. "Are chitosan formulations mucoadhesive in the human small intestine? An evaluation based on gamma scintigraphy" Intl J Pharm, 2006, vol. 307, pp. 285-291.
Salvador et al. "Continuous infusion versus bolus injection of loop diuretics in congestive heart failure (Review)" The Cochrane Collaboration, 2009.
Santus et al. "An in vitro-in vivo investigation of oral bioadhesive controlled release furosemide formulations" Eur J Pharm Biopharm, 1997, vol. 44, pp. 39-52.
Shin et al. "Enhanced dissolution of furosemide by coprecipitating or cogrinding with crospovidone" Intl J Pharm, 1998, vol. 175, pp. 17-24.
Sistovaris et al. "Multifunctional substances-Determinational of pKa-values by various methods" Fresnius J Anal Chem, 1991, vol. 340, pp. 345-349.
Terao et al. "Improvement in site-speci c intenstinal absorption of furosemide by Eudragit L100-55" J Pharm Pharmacol, 2001, vol. 53, pp. 433-440.
Thoma et al. "Photostabilization of drugs in dosage forms without protection from packaging materials" Intl J Pharm, 1991, vol. 67, pp. 169-175.
Van Der Watt et al. "The effect of mixing variables on the dissolution properties of direct compression formulations of furosemide" 1995, vol. 21, pp. 2047-2056.

* cited by examiner

*Primary Examiner* — James D Anderson
*Assistant Examiner* — William Lee
(74) *Attorney, Agent, or Firm* — Lawson & Weitzen, LLP; Sonia K. Guterman; Anna E. Stanford

(57) ABSTRACT

Diuretic bioactivity profiles of phase inversion micronized furosemide and furosemide co-precipitated with Eudragit L100, and mixtures of those formulations with stock furosemide, reduced or eliminated the rapid spike in diuresis associated with immediate release formulations and maintained cumulative urine output. Of the formulations tested, each of a mixture of micronized furosemide with stock furosemide, and Eudragit L100 polymer with stock furosemide demonstrated optimal diuretic bioactivity profiles in subjects.

26 Claims, 7 Drawing Sheets

COMPOSITIONS AND METHODS FOR LOOP DIURETICS WITH CONSISTENT BIOAVAILABILITY

RELATED APPLICATIONS

The present utility application claims the benefit of U.S. provisional application Ser. No. 61/376,737 filed Aug. 25, 2010, which is hereby incorporated herein by reference in its entirety.

TECHNICAL FIELD

The invention relates to formulations of a composition to contain a hydrophobic agent and a micronized phase inverted form of the hydrophobic agent, and methods regulating diuresis to decrease or eliminate diuretic spike.

BACKGROUND

Furosemide is a loop diuretic widely used to treat congestive heart failure (CHF) and other edematous conditions to rid the body of excess water, reduce blood pressure, and mobilize edemas. However, due to the narrow window of furosemide absorption, occurring in the proximal gastrointestinal tract, only immediate release oral formulations are clinically available. The most common pharmaceutical formulation of furosemide, LASIX®, a current diuretic for treating congestive heart failure (CHF), is absorbed only in the proximal small intestines [8]. Furosemide is a weak acid (pKa 3.9), and is protonated only in the acidic lumen of the stomach and proximal small intestines [23]. In the more distal gastrointestinal (GI) tract, furosemide becomes deprotonated and carries a negative charge that significantly reduces its ability to cross biological membranes [8]. Compounding the site specificity of absorption, furosemide has low water solubility leading to its classification as a class IV narrow absorption window therapeutic [16,26].

Accordingly, furosemide bioactivity is characterized by a sharp onset of diuresis ("the "Niagara effect") that occurs when furosemide blocks the sodium/potassium/chlorine (Na—K-2Cl) co-transporter (NKCC) in the thick ascending limb of the kidneys causing diuresis [11]. Bolus and continuous administration of furosemide in intravenous settings in patients experiencing severe CHF demonstrate that continuous administration at lower concentrations produced greater diuretic efficiency and reduced subsequent hospitalization rates. Congestive heart failure patients who are treated with Lasix experience rapid diuresis followed by an increase in water intake over the course of the day that leads to peaks and troughs in blood pressure and leads to development of patient tolerance (i.e., a decrease in efficacy) of Lasix that requires increased dosing as a function of the time period of course of treatment [12]. Current formulations of furosemide have bioactivity profiles that are inconvenient for patients, produce inefficient diuresis, and cause increased renal stress with dose escalation. Renal stress is associated with kidney failure later in life, and development of high blood pressure. There is a need for improved formulations of loop diuretics and other hydrophobic compounds.

SUMMARY

An aspect of the invention provides compositions and methods related to a micronized hydrophobic agent which have a variety of properties advantageous in treating edematous conditions and disorders. The methods of the invention form particles that have a size of at least about 1 micrometer which improves the bioactivity of the hydrophobic agent for administration to a subject. The improved bioactivity regulates diuresis in subjects, an advantage compared to current diuretics which cause excessive and inconsistent fluid loss.

An embodiment of the invention provides a pharmaceutical composition formulating a mixture of a hydrophobic agent, such as furosemide, and a phase inverted micronized form of the agent with an acceptable salt or buffer, wherein the composition has an average particle size of at least about 1 micrometer and is formulated as a unit dosage of a range selected from about 0.05 mg/kg (50 µg/kg), about 0.1 mg/kg (100 µg/kg), about 1 mg/kg, about 2 mg/kg, about 5 mg/kg, or about 10 mg/kg. The term "at least about 1 micrometer", as provided herein means about 1 µm to about 4 µm; about 1 µm to about 5 µm; about 2 µm to about 3 µm; about 2 µm to about 4 µm; about 2 µm to about 6 µm; about 3 µm to about 5 µm; and, about 3 µm to about 6 µm.

The hydrophobic agent in an embodiment is a loop diuretic selected from the group of: furosemide, azosemide, bumetanide, piretanide, torasemide, ethacrynic acid, etozolin, and a combination of these.

An aspect of the invention provides a method for formulating a micronized loop diuretic. A solution including the loop diuretic is combined with an excess of miscible non-solvent fluid, such as petroleum ether, such that the solvent: non-solvent ratio is selected from the range: 1:5, 1:10, 1:20, 1:40 and 1:100. The miscible non-solvent is selected from an ether, an alkane such as heptane and octane, an oil such as olive oil and soybean oil, and a chlorinated organic solvent such as trichloroethylene and methylene chloride. Combining the solution and non-solvent results in formation of a precipitate of the phase inverted loop diuretic in suspension. The suspension is collected, thereby formulating the micronized phase inverted loop diuretic, such that following micronization the phase inverted particle is at least about 1 µm in size. The term "at least about 1 µm", as provided herein means about 1 µm to about 4 µm; about 1 µm to about 5 µm; about 2 µm to about 3 µm; about 2 µm to about 4 µm; about 2 µm to about 6 µm; about 3 µm to about 5 µm; and, about 3 µm to about 6 µm. The suspension is collected by lyophilization. Alternatively, the suspension is collected by spray drying, solvent removal, solvent evaporation, vacuum concentration, reverse extraction, solute precipitation, dialysis, a combination of these or any micronization technique that results in a particle size of at least about 1 µm.

The loop diuretic solution includes a solvent selected from: ethyl acetate, methyl acetate, isopropyl acetate, benzyl acetate, butyl acetate, octyl acetate, amyl acetate, methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1-ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, di(ethylene glycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-pentanediol, and 3,5-pentanediol and a combination of these.

An aspect of the invention provides a method for regulating diuresis in a patient afflicted with an edematous condition or disorder, such as congestive heart failure, cirrhosis, epidemic dropsy, nephrotic syndrome, chronic kidney disease, malnutrition, and/or thyroid disease, such that the patient is administered an effective dosage of the pharmaceutical composition having greater bioavailability compared to current non-micronized loop diuretic treatment. The dosage is of a range selected from about 0.05 mg/kg (50 µg/kg), about 0.1 mg/kg (100 µg/kg), about 1 mg/kg, about 2 mg/kg, about 5 mg/kg, or about 10 mg/kg. Urine output is measured and monitored and is expelled at a consistent monotonic function of time such that cumulative urine output is maintained in comparison to urine production from treatment with current non-micronized loop diuretic treatment. Treatment of the pharmaceutical composition results in elimination or reduction of an initial diuretic spike of urine production ("Niagara effect") in the patient. The Niagara effect presents a problem for use of current diuretics due to discomfort, embarrassment, and even later development of adverse effects such as kidney function disorders.

An aspect of the invention provides a pharmaceutical composition which is a physical mixture of a solid dispersion of the non-micronized loop diuretic, such as furosemide, and a pH-altering, water-permeable polymer such as a Eudragit. The loop diuretic is selected from the group of: furosemide, azosemide, bumetanide, piretanide, torasemide, ethacrynic acid, etozolin, and a combination thereof.

Another aspect of the invention provides a method of formulating the pharmaceutical composition which is a physical mixture of a solid dispersion of loop diuretic, such as furosemide, and pH-altering polymer such as a Eudragit, wherein the non-micronized loop diuretic and the pH-altering, water-permeable polymer are mixed by weight into a homogeneous physical mixture. The loop diuretic is selected from the group of: furosemide, azosemide, bumetanide, piretanide, torasemide, ethacrynic acid, etozolin, and a combination thereof.

BRIEF DESCRIPTION OF THE DRAWINGS

FIG. 1 panel A is a set of scanning electron micrographs of each of stock furosemide (i), micronized furosemide (ii), and furosemide co-precipitated with Eudragit L-100 (iii) at 1,000× (top row) and 5,000× (bottom row) magnifications. Rod-like crystals shown in (i) are characteristic of stock furosemide [1]. The crystal size appears smaller in the micronized doses (ii) and more needle-like when co-precipitated with Eudragit L-100 (iii). A size bar is shown in each image. The measure of the bar is 30 µm for the top row and 6 µm for the bottom row. An exemplary crystal size is shown in each of the 5,000× images. Stock furosemide shown in bottom row of (i) has individual crystal length of ~5 µm. In the case of micronized furosemide, shown in the bottom row of (ii), individual crystal lengths are ~1 µm or less. Furosemide co-precipitated with Eudragit L-100, shown in the bottom row of (iii), has individual crystal length of ~5.2 µm.

FIG. 1 panel B is a tracing of heat flow as a function of temperature acquired by differential scanning calorimetry of oral furosemide doses. Stock (top tracing) and micronized furosemide (second tracing from top) thermally decompose at about 220° C. Eudragit L-100 undergoes glass-to-rubber transition at about 65° C. and melts at about 220° C. (middle tracing). Coprecipitation of Eudragit and furosemide (fourth tracing from top) or physical mixing of Eudragit and furosemide into a solid dispersion (bottom tracing), yielded the glass transition and melting temperature of L-100, and the polymer melt was overtaken by the thermal decomposition of furosemide, both occurring at about 220° C.

FIG. 1 panel C is a line plot of percent transmittance as a function of wavelength acquired by Fourier transform infrared spectroscopy of the same oral furosemide doses shown in the heat flow graphs in panel B. Stock and micronized formulations were observed to have nearly the same absorption pattern. Eudragit L-100 was observed to have a similar absorption to furosemide with the most notable exceptions of the additional peak at 1705 $cm^{-1}$ and lack of peaks at about 3400 $cm^{-1}$. Both the co-precipitated and physically mixed formulations show similar absorption patterns indicating that neither formulation yielded additional chemical bonds.

FIG. 3 panel A is a bar graph showing cumulative urine output and bioactivity profiles of each of a micronized furosemide (grey bar); a physical mixture, solid dispersion of equal parts stock furosemide and micronized furosemide (cross-hatch); and each of control basal (no treatment: solid bar); and control stock furosemide (open bar). The data for micronized furosemide show a statistically insignificant trend towards increased urine output compared to stock furosemide.

FIG. 3 panel B is a bar graph showing cumulative urine output and bioactivity profiles for each of: Eudragit L100 incorporated into oral furosemide doses by co-precipitation (solid bars); and a physical mix to form a solid dispersion (cross hatch). Eudragit L100 co-precipitated furosemide doses were observed to have a statistically insignificant trend towards increased cumulative urine output at hours 4-10, and decreased urine output at hour 2 compared to stock (open bar). Error bars depict standard error of the mean (s.e.m.).

FIG. 4 panel A is a bar graph showing cumulative urine output and bioactivity profiles of each of: a micronized furosemide (gray bars); a physical mixture, solid dispersion of equal parts stock and micronized furosemide (cross-hatch); control basal (solid bar); and control stock furosemide (empty bar). The data show that equal parts stock and micronized furosemide yielded a statistically insignificant trend towards increased urine output compared to stock furosemide.

FIG. 4 panel B is a bar graph depicting cumulative urine output and bioactivity profiles of each of: Eudragit L100 incorporated into oral furosemide doses by co-precipitation (solid bar); and a physical mixing to form a solid dispersion (cross hatch). The Eudragit L-100 co-precipitated doses were observed to yield a statistically insignificant trend towards increased cumulative urine output at all timepoints compared to stock. The 5 mg/kg doses produced greater urine output than 2.5 mg/kg doses. Error bars depict s.e.m.

FIG. 5 panel A is a bar graph showing cumulative urine output and bioactivity profiles of each of: a micronized furosemide (gray bars); a physical mixture, solid dispersion of equal parts stock and micronized furosemide (cross hatch); control basal (solid bars); and control stock furosemide (empty bars). The data show that with 10 mg/kg doses, the stock furosemide induced a statistically significant greater urine output at the time point of two hours after oral dosing than each of the micronized furosemide and the basal control ($p<0.01$, $N=3$). Increased urine output within the first two hours mimicked the Niagara effect experienced clinically, indicating that 10 mg/kg was the appropriate dose for testing the effectiveness of formulations to reduce the Niagara effect without reducing cumulative urine output 10 hours after administration. Administering either micronized furosemide or an equal parts mixture of stock and micronized furosemide resulted in less urine output than stock furosemide at two hours, and both produced similar cumulative diuresis by hour 10. The linearity of the bioactivity profile was greater for the mixture of each of stock and micronized furosemide ($R2=0.86$) than for micronized furosemide alone ($R2=0.83$); the mixture was accordingly chosen as the lead micronized formulation used in examples herein in further bioactivity testing.

FIG. 5 panel B is a bar graph showing cumulative urine output and bioactivity profiles of each of Eudragit L100 incorporated into oral furosemide doses by co-precipitation (solid bars) and a physical mixing to form a solid dispersion (cross hatch bars). The data show that co-precipitated furosemide and Eudragit L100 produced the greatest cumulative diuresis and also produced the greatest diuresis at hour 2. The result was observed to be statistically significant and greater than the output produced by each of the basal control subjects and the subjects dosed with the physically mixed solid dispersion of Eudragit L100 and the stock furosemide ($p<0.05$, $N=3$). Therefore, the co-precipitated dose produced a greater Niagara effect than stock furosemide. The physical mixture solid dispersion of equal parts Eudragit L100 and stock furosemide produced similar cumulative urine output at hour 10 and very little urine output at hour two. The solid dispersion physical mixture of Eudragit L100 and stock furosemide formulation was used in further testing in examples herein as it was characterized by linearity of the bioactivity profile ($R2=0.94$) and the results of the diuresis assay. Error bars depict s.e.m, *$p<0.05$, **$p<0.01$.

DETAILED DESCRIPTION

Figure 1A:
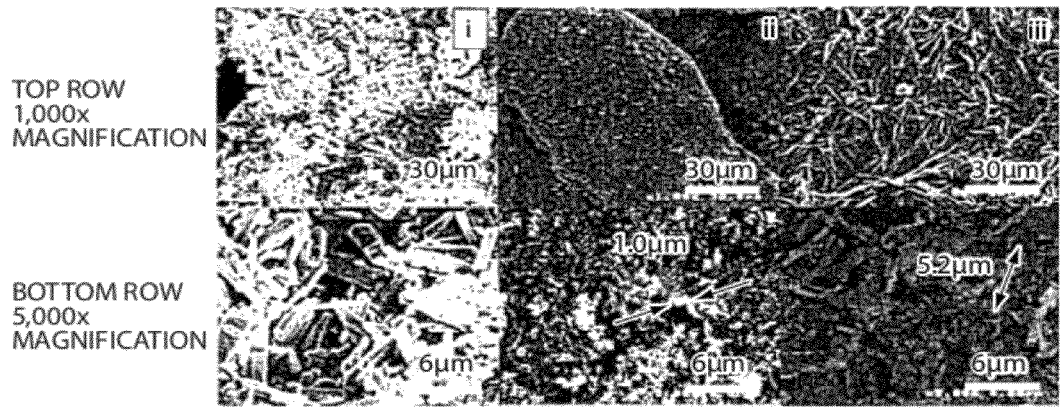
FIG. 1 contains scanning electron micrographs, differential scanning calorimeter curves and Fourier transform infrared spectroscopy (FTIR) tracings for characterizations of oral furosemide doses.

More than 5.8 million Americans currently are affected by CHF. Accordingly, a variety of controlled release formulations of furosemide have been tested with only limited success in developing a product with consistent bioactivity, i.e., effecting a steady rate of elimination of excess water as a function of time of dosage in a patient [3]. A comparison of continuous release intravenous (IV) administration of furosemide to bolus intravenous control patients demonstrates a benefit from continuous release. The resulting reduction in hospitalization of human patients shows the need for a controlled release formulation [10,20] having the convenience and economy of oral administration.

The primary obstacle to creating a controlled release furosemide formulation is its limited residence in the proximal GI. Gastroretentive delivery of furosemide was measured as a generalized mucoadhesive gastroretentive drug delivery system that relies on the mucoadhesion of a blend of carbomer and hydroxypropyl methyl cellulose first in a rabbit model and then in six healthy human volunteers [21]. An insignificant increase was observed in gastric residence time with bioadhesive formulations [21]. Bioadhesive microcrystalline chitosan was found to increase gastric residence time [18,19, 21].

A floating dosage form of furosemide was found to enhance bioavailability in six healthy human volunteers, and residence time of the floating pill was determined by radiography [17]. Each subject imbibed 100 ml of water hourly and while 100 ml of water hourly is not excessive during diuretic testing, it may affect the residence time of the floating pill within the stomach [17]. In the fasted state, very little fluid remains within the stomach, which has led to the irreproducibility and failure of previous floating pill studies [8]. Accordingly, these results are of questionable clinical relevance because of the prescribed drinking schedule [17]. Furosemide was formulated into a swelling gel that once ingested became too large to pass through the pyloric sphincter, resulting in gastric retention [8]. Phase II clinical results of a Furosemide GR™ formulation showed inconsistent reduction in urinary urgency in CHF patients. Depomed, Menlo Park, Calif.) tested a methacrylate-copolymer (Eudragit L-100-55) as a pH altering polymer for its ability to widen the absorption window of furosemide by lowering the pH in the distal GI [24]. Water solubility of furosemide was increased by co-grinding and co-precipitation with the hydrophilic polymer, crospovidone [22].

While gastric retention of furosemide has proven challenging, data in examples herein show that spherical crystallization and co-precipitation with pH-altering polymers have great potential to alter the diuretic profile of furosemide without requiring prolonged gastric residence. Examples herein show compositions and methods of utilizing micronization procedures such as phase inversion-based precipitation techniques in combination with GI pH-altering polymers, and blends with stock furosemide to reduce or eliminate the Niagara effect without reducing the total urinary output over a 10 hour period in a subject model.

The micronization procedure transforms the hydrophobic agent in its common form from a compound, which as delivered directly to a subject has low relative bioavailability. The transformed compound has a much higher relative bioavailability resulting from the micronized properties. Further, it is envisioned that the micronized agent is additionally processed to produce microparticles or to incorporate the agent into other drug delivery devices. Microparticles of the micronized hydrophobic agent are prepared by any of several common microencapsulation techniques. Suitable methods of encapsulation are selected to produce the desired physical and chemical properties of the encapsulant and the material to be encapsulated.

As used herein, the term "hydrophobic agent" refers to any hydrophobic compound including active agents and non-active agents. The hydrophobic agent does not adsorb water or absorbs a minimal amount of water. Hydrophobic agents include, but are not limited to, adhesives, gases, pesticides, herbicides, fragrances, antifoulants, dies, salts, oils, inks, cosmetics, catalysts, detergents, curing agents, flavors, foods, fuels, metals, paints, photographic agents, biocides, pigments, plasticizers, propellants and the like. The active agent also may be a bioactive agent.

The bioactive agent is a therapeutic material or composition, for example, adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastrointestinal motility effector; glucocorticoid; hair growth stimulant; hemostatic; histamine $H_2$ receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine Al antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor; anti-cancer, e.g., paclitaxel.

Encapsulation methods function to surround a therapeutic agent and to influence metabolism, release, and kinetics of absorption. Encapsulation methods include, but are not limited to, spontaneous emulsion, coacervation, solvent removal encapsulation, solvent evaporation encapsulation, phase separation encapsulation, and low temperature microsphere formation. Several of these methods also serve as a method of collecting the hydrophobic agent in suspension. Spontaneous emulsion is a self-emulsifying drug delivery system. Emulsions form when added to an excess of water without external vigorous mechanical dispersion or agitation. The method results in gentle handling of the bioactive agents and stability of unstable or hydrophobic agents. Coacervation involves the phase separation of a liquid precipitate, or phase, when solutions of two hydrophilic colloids are mixed under suitable conditions. The method produces tiny spherical droplets of organic molecules, which are held together by hydrophobic forces from a surrounding liquid. The tiny spheres, which are 1 to 100 μm (micron, micrometer) in diameter, possess osmotic properties and form spontaneously from certain dilute organic solutions. Solvent removal includes a number of different methods including, but not limited to, evaporation, vacuum concentration, lyophilization, reverse extraction, solute precipitation, and dialysis.

The term "phase inversion", as used herein, refers to physical phenomena by which an agent dissolved in a continuous phase solvent inverts into a solid suspension in which the agent is the continuous phase. This can be obtained by any of several methods: removal of solvent (e.g., evaporation; also known as dry process), addition of another species, addition of a solvent or addition to a non-solvent (also known as wet process). The wet process, which is used herein, has the agent solution poured or extruded into a non-solvent bath, in which the non-solvent and solvent are miscible. A phase inversion and the spontaneous formation of discreet microparticles, including nanospheres, is produced by using solvent and non-solvent pairs that are miscible with a greater than ten-fold excess of non-solvent. A continuous phase of non-solvent with dissolved agent incorporated is rapidly formed.

The phrase "miscible non-solvent", as used herein, refers to a characteristic of a liquid which is not a solvent for the solute, and which forms a homogeneous solution when mixed with a solvent. Combining the two miscible liquids results in a liquid that is homogeneous. Combining the two miscible liquids, if one is a solution of the solute, yields a precipitate.

The phrase "edematous condition or disorder, as used herein, refers to an abnormal accumulation of fluid beneath the skin or in one or more cavities of the body. Generally, the amount of interstitial fluid is determined by the balance of fluid homeostasis, and increased secretion of fluid into the interstitium or impaired removal of this fluid is associated with the edematous condition.

The term "Niagara effect", as used herein, refers to an initial diuretic spike experienced by a subject characterized by a sudden and heavy loss of fluid and production of urine which is a commonly observed accompanying administration of prior art diuretic agents. The term "subject" as used herein includes vertebrate animals such as mammals including humans, and birds, and reptiles. Subjects may be patients presenting with a disease condition or normal, and include experimental animals, agricultural animals, and high value animals such as zoo animals.

The term "diuresis", as used herein, refers to excessive urine production associated with treatment with a diuretic agent.

The phrase "physical mixture solid dispersion", as used herein, refers to formulations in which the drugs are homogeneously dispersed within a carrier. The methodology to make these solid dispersions includes co-fusion, physical mixing, co-dissolution in a proper solvent or a combination of them. A solid dispersion as prepared herein is physically mixed by stirring or other methods.

The phrase "water-permeable", as used herein, refers to a polymer in which water enters through an outer surface of the polymer, which does not solubilize in water.

The phrase "pH-altering polymer", as used herein, refers to a polymer, which acts locally to adjust the pH, for example, adjust the pH of a portion of the GI tract. A pH-altering polymer is selected herein to act locally and not throughout an entire length of the GI tract.

Additional embodiments and examples of the invention are found in the examples and claims below, which are illustrative and are not to be construed as further limiting. The contents of all literature cited herein are hereby incorporated in their entirety by reference.

Pharmaceutical Compositions

In one aspect of the present invention, pharmaceutical compositions are provided, wherein these compositions comprise a hydrophobic agent in micronized form, and optionally comprise a pharmaceutically acceptable carrier. In certain embodiments, these compositions optionally further comprise one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences* Ed. by Gennaro, Mack Publishing, Easton, Pa., 1995 (the contents of which are hereby incorporated by reference), discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Therapeutically Effective Dose

In yet another aspect, according to the methods of treatment of the present invention, a consistent diuretic bioactivity is promoted by contacting subject, for example having an edematous condition (hypervolumia) with a pharmaceutical composition as described herein. Thus, the invention provides methods for the treatment of edematous conditions comprising administering a therapeutically effective amount of a pharmaceutical composition comprising active agents that include the formulated hydrophobic agent, viz., the formulated micronized loop diuretic, to a subject in need thereof, in such amounts and for such time as is necessary to achieve the desired result. It will be appreciated that this encompasses administering an inventive pharmaceutical as a therapeutic measure to promote the consistent dieresis without a spike in fluid excretion known as the Niagara effect. In certain embodiments of the present invention a "therapeutically effective amount" of the pharmaceutical composition is that amount effective for promoting the consistent rate of fluid excretion. The compositions, according to the method of the present invention, may be administered using any amount and any route of administration effective for promoting the consistent rate of diuresis. Thus, the expression "amount effective for promoting the re-epithelialization of a wound", as used herein, refers to a sufficient amount of composition to promote consistent rate of diuresis as monitored as amount of fluid excretion as a function of time, and total amount of excretion during the time of monitoring. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., extent of edema or hypervolemia; age, weight and gender of the patient; diet, time and frequency of administration, drug combinations, reaction sensitivities, and tolerance/response to therapy. The formulated pharmaceutical compositions might be administered every day, several times a day, every other day, every 3 to 4 days, every week, or once every two weeks depending on half-life and clearance rate of the particular formulation. A preferred dosage schedule is daily oral administration.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially in animal models, usually mice, rats, rabbits, dogs, pigs, or primates. The animal model is also used to achieve a desirable concentration range and route of administration. Such information can then be used to determine useful doses and routes for administration in humans. A therapeutically effective dose refers to an amount of active agent that ameliorates the symptoms or condition. Therapeutic efficacy and toxicity of active agents can be determined by standard pharmaceutical procedures in experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from animal studies are used in formulating a range of dosage for human use.

Administration of Pharmaceutical Compositions

After formulation with an appropriate pharmaceutically acceptable carrier in a desired dosage, the pharmaceutical compositions of this invention can be administered to humans or to other mammals as powders, ointments, or drops, by any route including without limitation orally, rectally, parenterally, intracisternally, intravaginally, intraperitoneally, bucally, ocularly, or nasally, depending on the severity and location of the edematous condition being treated.

Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. Administration may be therapeutic or it may be prophylactic. The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions that are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions, which can be used include polymeric substances and waxes.

Uses of Pharmaceutical Compositions

The hydrophobic compositions herein for example the loop diuretic formulations are used to treat edema, identified as observable swelling from fluid accumulation in body tissues. Edema most commonly occurs in the feet and legs, where it is referred to as peripheral edema. The swelling is the result of the accumulation of excess fluid under the skin in the spaces within the tissues. In various hypervolemic diseases or edemas, excess fluid can accumulate in either one or both of the compartments of the connective tissue around the cells and blood vessels known as the interstitium and the blood vessels. The formulations herein treat accumulation of fluid in the interstitial air spaces (alveoli) in the lungs occurs in conditions such as pulmonary edema, and in what is called the third space, including cavities in the abdomen and in the chest (pleural effusion). The term, "anasarca" refers to severe, widespread accumulation of fluid generally throughout tissues and cavities of the body and the formulations herein are useful also in treating this condition. While the formulations herein of furosemide and other loop diuretics are useful to treat edema resulting from congestive heart failure (CHF), a widespread edematous condition, these formulations are also useful for treating edemas resulting from other etiologies including kidney failure, high blood pressure, excessive weight gain for example during pregnancy, and esophageal rupture and pancreatic disease.

A portion of these examples are published in an article entitled: "Diuretic Bioactivity Optimization of Furosemide in Rats" by Bryan Laulicht, Anubhav Tripathi, and Edith Mathiowitz; European Journal of Pharmaceutics and Biopharmaceutics 2011 (in press), doi: 10.1016/j.ejpb.2011.04.014 which is hereby incorporated herein by reference in its entirety.

EXAMPLES

Example 1

Loop Diuretic Micronization by Phase Inversion

Furosemide (Sigma Aldrich, St Louis, Mo.) was dissolved in ethyl acetate (Fluka, St Louis, Mo.) at a concentration of 4 mg/ml, near its maximum solubility. The furosemide solution was poured into an excess of miscible non-solvent, petroleum ether (Sigma Aldrich, St Louis, Mo.), at a volume ratio of 1:20 ethyl acetate to petroleum ether causing phase inversion of the furosemide [6]. Once phase inverted, the petroleum ether suspension was filtered using a Millipore stainless steel filter column (Billerica, Mass.) fitted with a 0.2 μm mixed cellulose ester filter membrane (Millipore. Billerica, Mass.). The furosemide retentate was then transferred on the membrane into 50 ml conical tubes topped with Kimwipes (Kimberly-Clark, Mississaua, Ontario) held in place by rubber bands and wrapped in aluminum foil to reduce light exposure. The phase inverted furosemide was placed inside a lyophilization jar (VirTis, Gardiner, N.Y.) and lyophilized for 24 hours until the powder was fully dried. Dried powder was separated from the filter membrane and stored in amber glass containers to minimize light-induced degradation [25].

Example 2

Co-precipitation of Loop Diuretic with Eudragit L100

Furosemide was dissolved in ethyl acetate as in the precipitation procedure (Example 1) and then mixed with 1 w/v % Eudragit L100 (Rohm GmbH, Dallustadt, Germany) pH-sensitive, acrylic acid derived polymer in ethanol (Sigma Aldrich, St Louis, Mo.) to create a 1:1 dissolved mass ratio of furosemide to Eudragit. The furosemide and Eudragit solution was poured into an excess of petroleum ether (Sigma Aldrich, St Louis, Mo.), a non-solvent for both furosemide and Eudragit, leading to co-precipitation of the polymer and drug. After co-precipitation, the polymer and drug were filtered and lyophilized as with phase inversion micronized furosemide (Example 1). Eudragit L100 has a pKa of 6.0, and at small intestinal pH>6.0, local release of protonated carboxylic acid residues liberates hydrogen ions thereby reducing pH as the polymer dissolves [7,9,13,15].

Example 3

Scanning Electron Micrograph (SEM) Analysis of Loop Diuretic Doses

Conductive, double-sided carbon tape was overlaid on top of aluminum SEM stubs. Dry powder samples of stock furosemide, phase inversion micronized furosemide, and co-precipitated furosemide and Eudragit L100 were transferred onto the carbon tape. The SEM stubs were then sputter coated with 50 Å to 100 Å of gold-palladium (Emitech K550, Kent, UK). Each stub was imaged by SEM (Hitachi S-2700, Tokoyo, Japan) with an accelerating voltage of 8 kV. The electron beam was aligned and digital images were obtained at 1,000× and 5,000× (Quartz Imaging Corporation, Vancouver, BC).

Example 4

Differential Scanning Calorimetry (DSC) Analysis of Loop Diuretic Doses

Three to five milligrams of each furosemide powder dosage form was weighed in aluminum sample pans (Perkin-Elmer, Waltham, Mass.). Each sample was covered with an aluminum lid (Perkin-Elmer, Waltham, Mass.) and crimped to seal the sample within the pan (Perkin-Elmer, Waltham, Mass.). Sealed pans were then placed into a DSC7 (Perkin-Elmer, Waltham, Mass.), controlled by Pyris software (Perkin-Elmer, Waltham, Mass.). Samples were cooled to −25° C. then heated to 250° C. and compared to an empty reference pan to quantify heat flow as a function of sample temperature during thermal transitions.

Example 5

Fourier Transform Infrared Spectroscopy (FTIR) Analysis

Infrared transmittance of the powdered furosemide samples was measured using total internal reflectance FTIR (Spectrum One, Perkin Elmer, Waltham, Mass.). Absorption peaks were labeled using Spectrum software (Perkin Elmer, Waltham, Mass.). Infrared (IR) spectra were analyzed to evaluate the presence of functional groups.

Example 6

Dose Preparation for Animal Model Subjects

Subject rats were weighed at the start of each example. Each formulation was prepared and then loaded into size 9 gelatin capsules using a gelatin capsule filler (Torpac, Fairfield, N.J.). Each gelatin capsule was weighed on a microbalance (AD-4 Autobalance, Perkin Elmer, Waltham, Mass.) prior to and after drug loading to prepare oral doses of 2.5 mg, 5 mg, or 10 mg of drug per kg of body mass within 0.5 mg of dose mass.

Example 7

Oral Administration to Animal Model Subjects

Each subject was anesthetized in an induction chamber with 3.5% isoflurane (Novation, Irving, Tex.) for 5-10 minutes. Once anesthetized, the subject was removed from the induction chamber and dosed with a size 9 gelatin capsule containing one of the furosemide formulations using the gelatin capsule dosing syringe (Torpac, Fairfield, N.J.). As a negative control the same subjects were administered empty gelatin capsules without furosemide to quantify the basal urine mass output for comparison. Upon recovery from anesthesia, each subject was then transferred to a metabolic cage for urine collection over a 10 hour period.

Example 8

Diuretic Bioactivity Analysis

Figure 2:
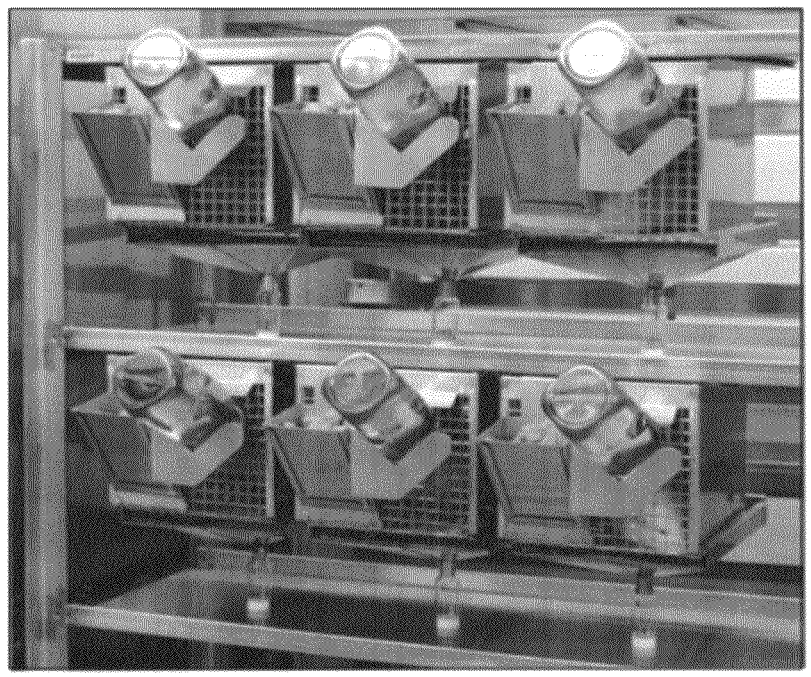
FIG. 2 is a photograph of subjects housed in a metabolic cage rack to obtain data for non-invasive quantification of urine output without anesthesia or handling.

Twelve albino, male, Sprague-Dawley subjects (450 g to 750 g) were used as subjects in the bioactivity analysis example. Subjects were housed in standard bedded cages in accordance with NIH and IACUC guidelines. Immediately after oral gavage with a furosemide formulation, subjects were housed individually in a metabolic cage rack (Unifab Cages, Kalamazoo, Mich.) as shown in FIG. 2. Subjects were given access to food and water ad libitum throughout the study. Metabolic cages were equipped with wire grating floors that allowed for free passage and collection of excreted material during the period of containing the subject. Feces were collected beneath the large opening wire grating floor by smaller opening wire mesh screen, and urine continued through the screen into a funnel for collection into pre-weighed glass scintillation vials (Cole-Parmer, Vernon Hills, Ill.). At two hour intervals after dosing, the glass scintillation vials were weighed (Mettler Toledo, Columbus, Ohio) to quantify urine output as a function of time and were then replaced. Increased urine output above baseline values was used as a non-invasive measure of diuretic activity of the various furosemide formulations examined. After each 10 hour study, subjects were housed in bedded cages for a recovery period of at least 48 hours between metabolic cage studies.

Example 9

Strategy to Prepare Formulations to Obtain Consistent Diuresis by Loop Diuretics Formulated Herein It is contemplated herein that an ideal linear urine mass output as a function of time would reduce the Niagara effect, increase diuretic efficiency, and reduce renal stress without requiring gastric retention. To achieve this ideal, several approaches to prepare formulations were tested in examples herein: reducing particle size of furosemide, blending furosemide with pH-sensitive polymers, and combining both approaches by mixing each with unaltered stock furosemide.

Example 10

Loop Diuretic Dose Physiochemical Analysis for Alteration of Crystal Structure

Figure 1B:
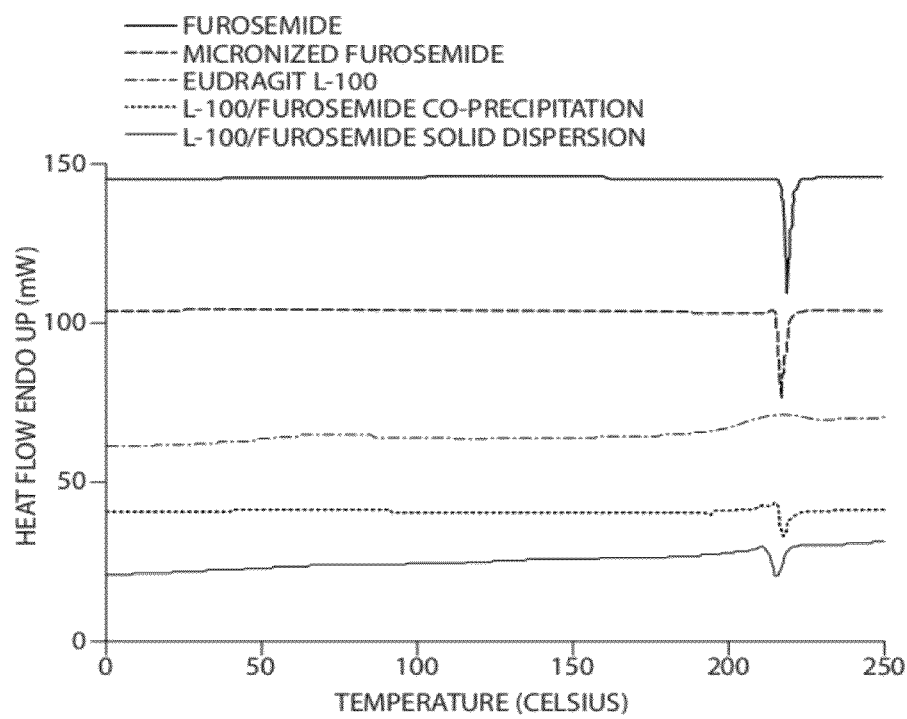
Figure 1C:
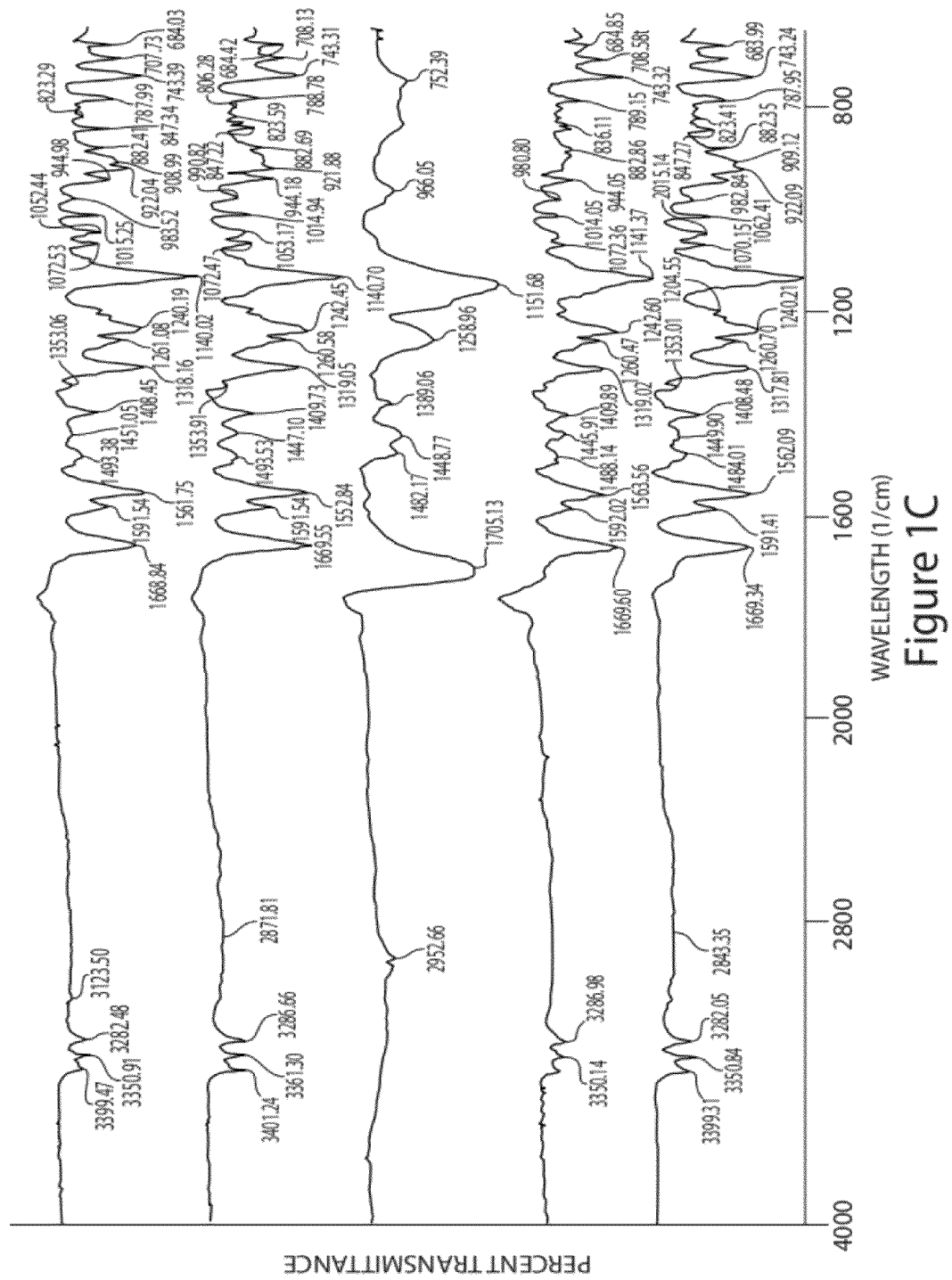

Scanning electron microscopy (SEM) was used to observe the angular, crystalline nature of stock pharmaceutically available furosemide. Individual crystals with length of at about 5 µm were observed (FIG. 1 panel A, i). Image analysis showed that phase inversion of furosemide alone decreased the majority of crystal lengths, or micronized the furosemide, from at about 5 µm in the stock formulation to less than 1 µm (FIG. 1 panel A, ii). Co-precipitation of furosemide with Eudragit L100 in equal masses resulted in a structure having a more needlelike crystal formation than the control stock furosemide (FIG. 1 panel A, iii). SEM data showed that furosemide dissolved in methanol and phase inverted by evaporation also resulted in reduced crystal size [1].

Differential scanning calorimetry (DSC) showed that the thermal decomposition temperature of stock furosemide, 217° C., was unchanged by phase inversion micronization (FIG. 1 panel B) [5]. Eudragit L100, as a thermoplastic polymer, exhibits a glass transition temperature at 65° C. and a melting temperature at 220° C. Without being limited by any particular theory or mechanism of action, due to the similarity of the thermal decomposition temperature of furosemide and the melting temperature of L100, mixed formulations showed the beginning of an endothermic melting transition interrupted by the exothermic decomposition. Both the coprecipitated and physically mixed solid dispersion of furosemide and Eudragit L100 demonstrated very similar thermal behavior indicating that neither co-precipitation nor physical mixing yielded covalent bonding.

FTIR analysis of phase inversion micronized furosemide showed no substantial difference from stock furosemide (FIG. 1 panel C). Eudragit L100 has a broad peak at 1705 $cm^{-1}$, corresponding to carbonyl stretching that is not present in either the co-precipitated or physically mixed formulations. Disappearance of the carbonyl peak indicates possible interaction and stabilization by the amine group of the furosemide. Both solid dispersion and precipitation of furosemide with Eudragit R/L-100 showed a loss of the amine peak at 3400 $cm^{-1}$ and translation of the 1900 $cm^{-1}$ carbonyl peak indicating a secondary interaction between the quaternary ammonium groups of Eudragit RJL-100 and the carbonyl groups of furosemide [1].

Each of the furosemide formulations herein were then administered at varying doses alone and mixed with stock furosemide. Data were compared to basal urine output and to urine output of subjects treated with control stock furosemide, to quantify changes in the bioactivity profiles resulting from the physiochemical alterations induced by phase inversion.

Example 11

Oral Diuretic Dose Escalation

Subjects were orally administered gelatin capsules containing furosemide doses and were housed in metabolic cages to obtain isolation of urine and its collection every two hours for a total of 10 hours, to quantify the extent that phase inversion micronized furosemide and Eudragit L100 mixtures with furosemide altered urine output compared to stock furosemide. Each dose was administered to three subjects and the average urine mass produced in the two hour time periods was determined and was compared to the average output of the same subjects that received a sham dosage without any furosemide, referred to in the figures as the basal output.

Figure 3A:
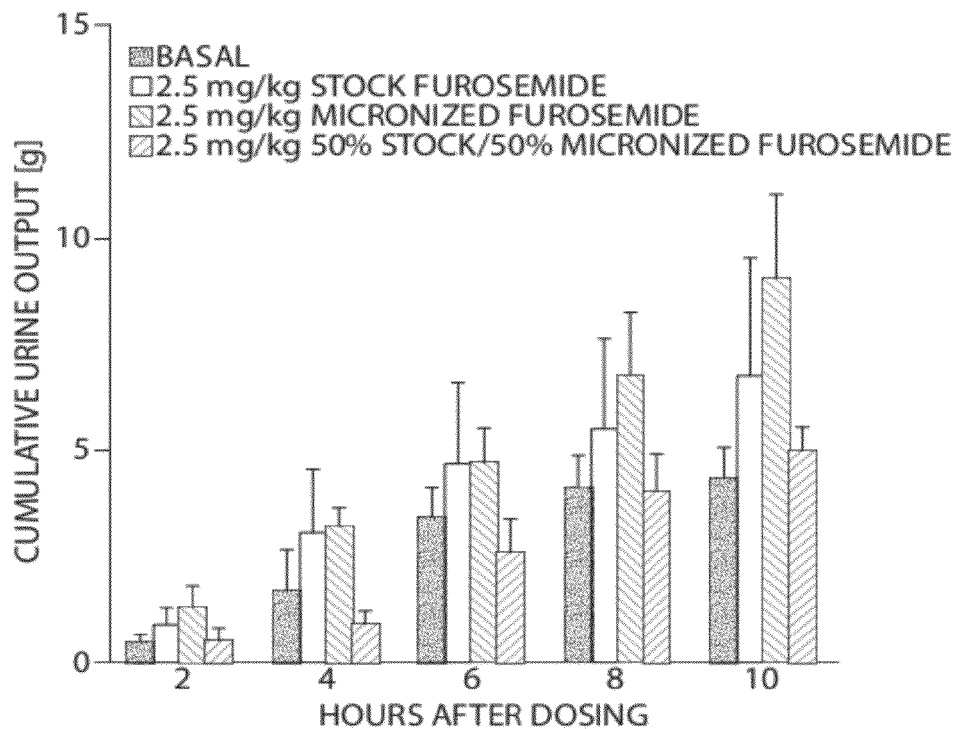
FIG. 3 is a set of bar graphs showing cumulative bioactivity response of subjects to each of: 2.5 mg/kg micronized and Eudragit L100-incorporated oral furosemide doses, and compared to stock furosemide (N=3).
Figure 3B:
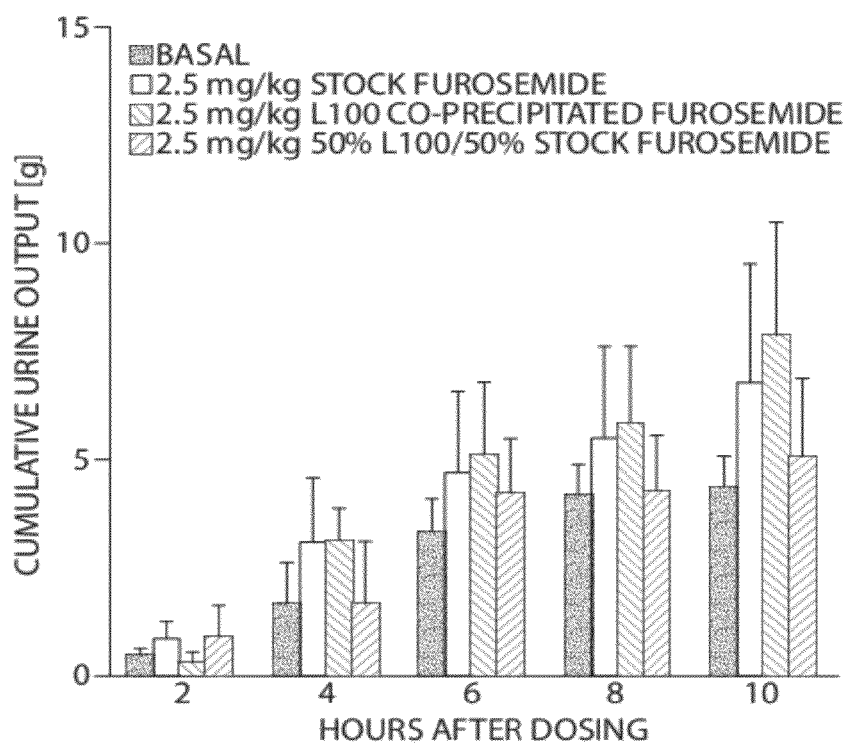
Figure 4A:
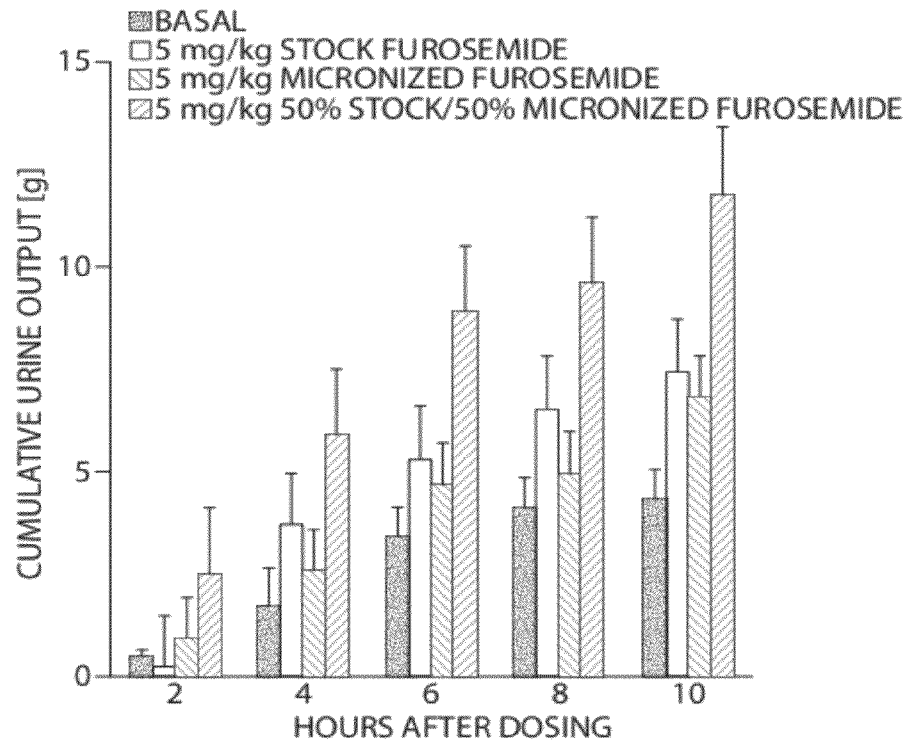
FIG. 4 is a set of bar graphs showing cumulative bioactivity response to each of: 5 mg/kg micronized furosemide, Eudragit L100-incorporated oral furosemide doses; and control stock furosemide (N=3).
Figure 4B:
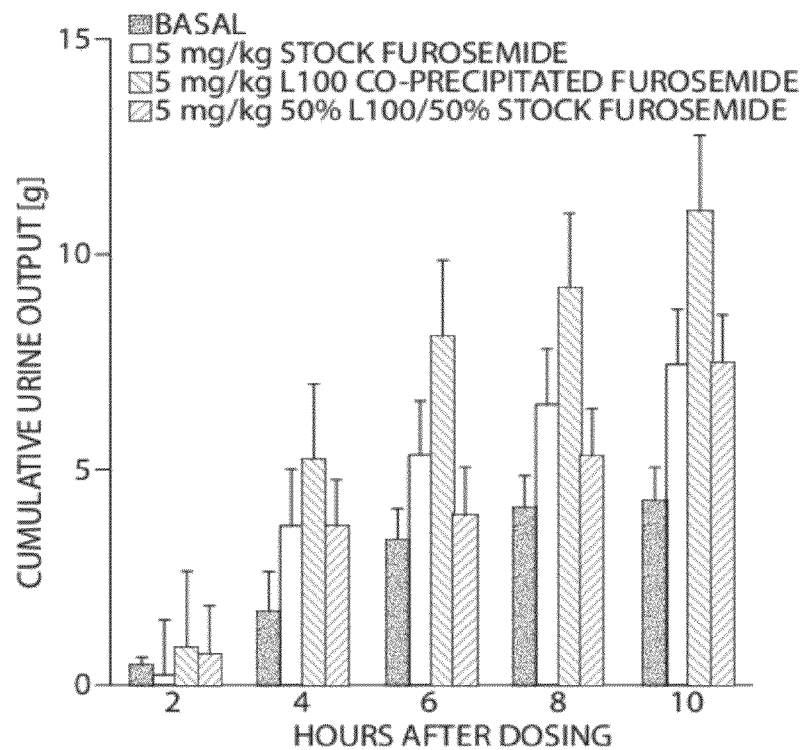

To determine the minimum necessary dose required to sufficiently emulate the Niagara effect, a dose escalation study was performed. The bioactivity profile of stock furosemide was compared to that of micronized furosemide and an equal parts mixture of stock and micronized furosemide. Additionally, the bioactivity response of stock furosemide was compared to that of furosemide co-precipitated with Eudragit L100, and to a mixture of equal parts of stock furosemide and co-precipitated furosemide with Eudragit L100, and to a physically mixed, solid dispersion of equal parts stock furosemide and Eudragit L100. All furosemide formulations produced greater cumulative urine output 10 hours after dosing than basal output at each of doses 2.5 mg/kg (FIG. 3) and 5 mg/kg (FIG. 4). Additionally, 5 mg/kg doses produced greater urine output than 2.5 mg/kg doses. However, the trends were statistically insignificantly different from basal output ($p>0.05$) indicating that higher furosemide dosing was required to mimic the bioactivity profile observed in humans.

Figure 5A:
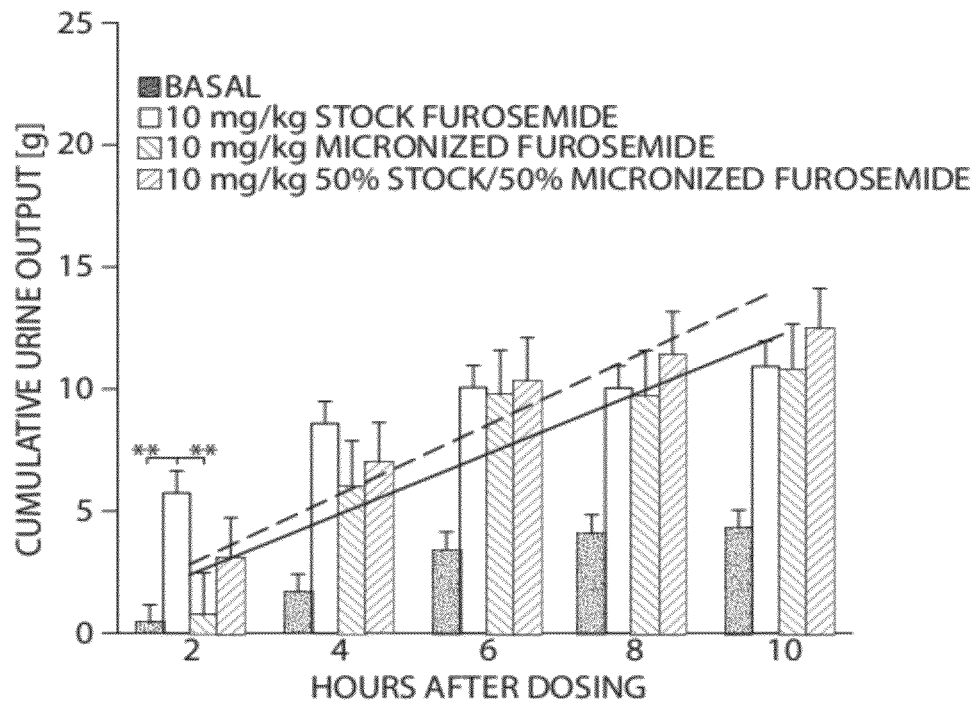
FIG. 5 is a set of bar graphs comparing bioactivity in response to each of: 10 mg/kg oral doses of micronized furosemide; and Eudragit L-100 mixed formulations of furosemide.
Figure 5B:
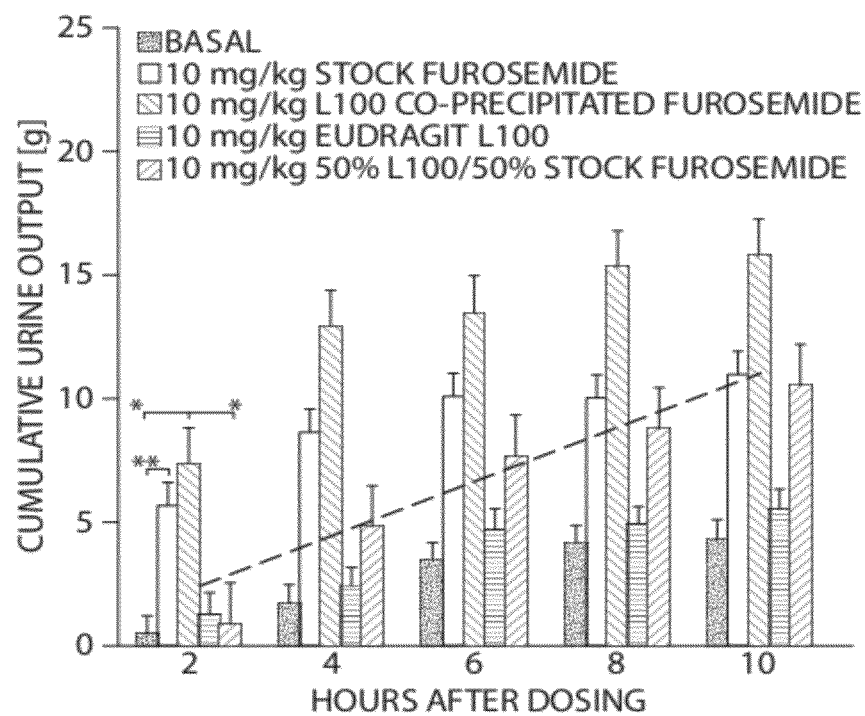

Increase of dosage to 10 mg/kg (N=3) resulted in the mean urine mass output two hours after dosing that was statistically significant: 12.2-fold greater than that of basal urine output, and 8.6-fold greater than the output produced after administration of an equivalent dose of micronized furosemide ($p<0.01$). The sharp increase in urine production observed two hours following administration of 10 mg/kg furosemide was observed to mimic the Niagara effect reported in clinical use. The cumulative urine output at hour 10 associated with administration of stock and micronized furosemide doses were not significantly statistically different, the stock furosemide producing 1.02-fold the total urine output of the micronized dose (FIG. 5 panel A). Therefore, the micronized furosemide dose demonstrated similar diuretic activity without the Niagara effect in hour two. However, the increase in cumulative urine output in hour four of the micronized dose indicated that micronization alone merely delayed the Niagara effect.

To test whether the delay in the Niagara effect was produced by micronization, combinations of stock furosemide and micronized furosemide were mixed at lower doses to produce a combined effect of maintaining diuresis while reducing the Niagara effect. Equal parts mixture of stock and micronized furosemide were observed to demonstrate 47% less urine output at hour two than stock furosemide and to maintain a consistent bioavailability profile, viz., a more linear cumulative urine output profile ($r2=0.86$) than the micronized dose alone ($r2=0.83$).

Phase inversion micronization reduced crystal size compared to stock, and resulted in re-crystallization of dissolved furosemide in the hydrophobic non-solvent, petroleum ether. Crystallization of furosemide in hydrophobic media may yield a more hydrophobic molecular organization to minimize interfacial energy with the non-solvent. Therefore, although phase inversion reduced particle size it may also have increased hydrophobicity leading to delayed water dissolution that corresponds to the delayed onset of pharmacological action.

With the administration of co-precipitated and solid dispersion furosemide and Eudragit L100 doses at 10 mg/kg, the co-precipitated dose were observed to produce 1.28-fold the diuresis at two hours than the stock furosemide (FIG. 5 panel B). The addition of L100 may have temporarily locally reduced pH, increasing the amount of time that the furosemide spends in the protonated state. Furosemide in the protonated state is more apt to cross biological membranes than the anionic, deprotonated form. L100 may also act as a bioadhesive promoting prolonged intimate contact of furosemide with the GI mucosa as the crystals hydrate and dissolve. As a control, administering 10 mg/kg of L100 alone was observed to not significantly increase urine output above basal levels indicating that the polymer alone had little or no effect on diuresis. The physical mixture of equal parts stock furosemide and L100 produced 0.15-fold the mean urine output of stock furosemide at two hours and 0.96-fold the mean cumulative diuresis after 10 hours of stock furosemide. The diuretic activity profile was observed to be even more linear ($r2=0.94$) than that of the mixture of each of stock and micronized furosemide.

Example 12

Optimization of Diuretic Bioactivity

Figure 6:
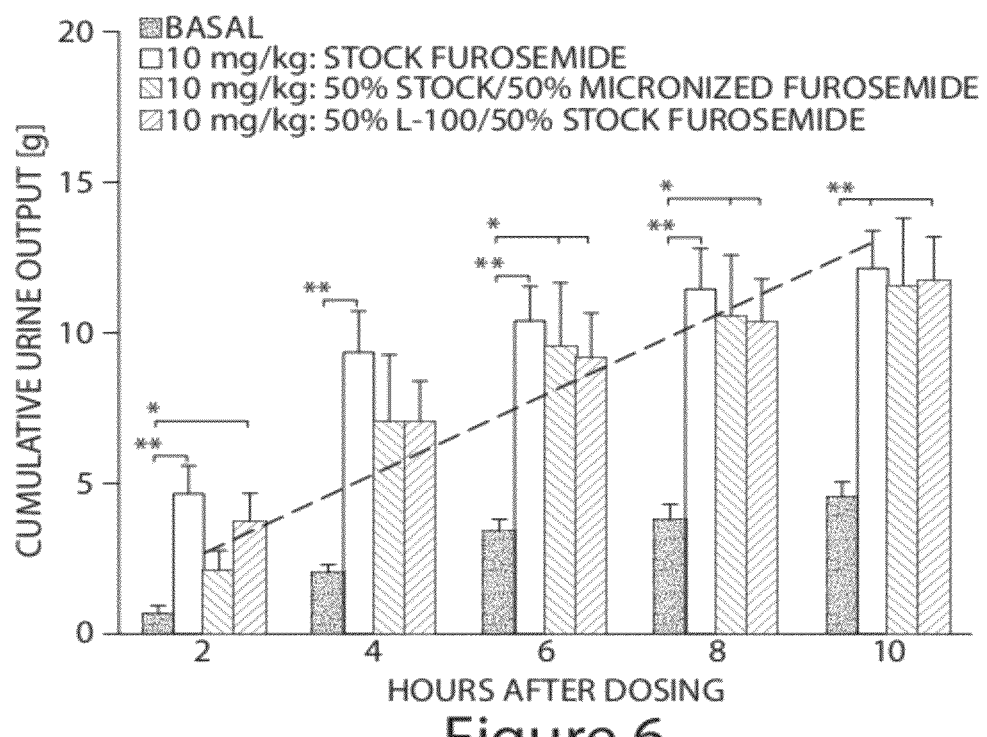
FIG. 6 is a bar graph showing bioactivity response of further testing of the lead formulations: each of micronized furosemide and Eudragit L100-incorporated oral furosemide dose candidates. Data herein used a larger number of subjects ($N=9$) per group, tested to determine the optimal oral furosemide formulation that would reduce the Niagara effect, and would maintain cumulative diuresis at 10 hours. Each of the mixture of equal parts micronized furosemide and stock furosemide (gray cross-hatch), and the physical mixture solid dispersion of Eudragit L100 and stock furosemide, produced less urine output than stock furosemide alone (empty bars) at hour two, indicating a reduced Niagara effect, and each of these formulations yielded a similar cumulative urine output at hour 10. The mixture of stock furosemide and micronized furosemide produced less urine output at hour two and was observed to have a more linear bioactivity profile ($R2=0.85$) than the Eudragit L100/stock furosemide mixture ($R2=0.78$). Therefore, the mixture of stock furosemide and micronized furosemide was chosen as the formulation which presents the optimal diuretic bioactivity observed herein. Error bars depict s.e.m, *$p<0.05$, **$p<0.01$.

The two lead candidate formulations, 10 mg/kg of an equal parts mixture of stock and micronized furosemide and a solid dispersion of equal parts stock furosemide and Eudragit L100, were administered to six additional subjects for a total of N=9, to directly compare the doses using a larger cohort (FIG. 6). Both formulations continued to demonstrate reduced diuresis compared to control stock furosemide at hour two and similar diuresis to control stock furosemide at hour 10. The mixture of each of stock furosemide and micronized furosemide produced less of a Niagara effect than the stock furosemide and Eudragit L100 mixture, and a 0.56-fold amount of the mean urine output was observed at hour two. Additionally at hour 10, the mixture of each of stock furosemide and micronized furosemide produced 0.95-fold the cumulative diuresis of the same dose of stock alone.

It was observed that the diuretic profile of the stock and micronized mixture ($r2=0.85$) was more linear than the mixture with L100 ($r2=0.78$), i.e., had a consistent diuretic bioactivity as a function of time. By the established parameters for the optimal bioactivity profile, the equal parts mixture of stock and micronized furosemide performed the best of formulations tested herein, followed by the equal parts mixture of stock furosemide and Eudragit L100.

Example 13

Clinical Potential of Bioactivity Optimized Oral Furosemide

Physiochemical analysis by FTIR and DSC indicates that furosemide did not undergo a chemical change in response to phase inversion micronization, co-precipitation with Eudragit L100, or physical mixing with Eudragit L100. Therefore, the safety master file from the widely clinically used furosemide should apply to the described doses. The lack of a spike in urine output within two hours of oral administration observed in each of the equal parts mixture of stock and micronized furosemide, and the equal parts mixture of Eudragit L100 and stock furosemide, is an indication of clinical potential. Unlike previous data regarding bioavailability of 15 mg/kg aqueous furosemide solution co-administered with 400 mg/kg aqueous Eudragit L100-55 solution [24], the orally administered doses herein contain at most 10 mg/kg Eudragit polymer. While Eudragit polymers are well-tolerated in clinical practice, minimizing Eudragit incorporation is important in a clinical, daily dosing regimen. Additionally, the previously reported data utilized an isolated loop such that the pH of the entire loop was significantly altered by the incorporation of Eudragit L100-55 [24]. Furosemide was delivered orally in a gelatin capsule with little Eudragit L100 polymer and therefore was unlikely to significantly alter the pH of a large segment of the intestines. Physical bonding is envisioned herein to occur between the carbonyl groups of the Eudragit L100 and the amine groups of furosemide promoting physical proximity within the intestines. The Eudragit L100 may locally reduce pH and supply hydrogen ions to protonate furosemide at higher pH than the drug alone [15]. Additionally, the temporary bioadhesiveness of Eudragit L100 prior to its dissolution as an acrylic acid derived polymer may serve to promote intimate contact of the furosemide with the absorptive epithelium [14,21].

Furosemide and Eudragit R/L-100 administered to humans reduced the Niagara effect at a dose of constant mass dose of 40 mg of furosemide in healthy human volunteers [2]. However, the cumulative urine output 10 hours after oral administration was only about 53% of the stock furosemide dose. Therefore, higher furosemide doses would be required to achieve the same diuretic efficiency. If the bioactivity profile translates from the small animal trials conducted in examples herein, the described doses have the potential to reduce the Niagara effect and maintain diuretic efficiency obviating the need for higher doses to achieve similar diuresis.

Examples herein show that each of mixtures of phase inversion micronized and stock furosemide, and Eudragit L100 and stock furosemide, reduced the Niagara effect and maintained diuretic efficiency in subjects. Moreover, mixed doses reduced the Niagara effect, and produced similar cumulative urine output 10 hours after oral administration as compared to stock furosemide alone. If the optimal bioactivity profile observed in subjects, produced by mixtures of stock furosemide with micronized furosemide or Eudragit L100, translates to larger animals and humans it may improve diuretic efficiency, reduce the risk of ototoxicity, and ameliorate concerns of acute tolerance currently associated with clinical use of furosemide.

REFERENCES

1. J. M. Aceves, R. Cruz, E. Hernandez, Preparation and characterization of Furosemide-Eudragit controlled release systems. Int. J. Pharm. 195 (2000) 45-53.
2. O. Al Gohary, S. El Gamal, Release of Furosemide from Sustained-Release Microcapsules Prepared by Phase-Separation Technique. Drug Dev. Ind. Pharm. 17 (1991) 443-450.
3. American Heart Association. 2000 heart and stroke statistical update. Dallas (TX): American Heart Association, 1999.
4. P. L. Bardonnet, V. Faivre, W. J. Pugh, J. C. Piffaretti, F. Faison, Gastroretentive dosage forms: Overview and special case of *Helicobacter pylori*. J. Controlled Release 111 (2006) 1-18.
5. H. Beyers, S. F. Malan, J. G. van der Watt, M. M. de Villiers, Structure-solubility relationship and thermal decomposition of furosemide. Drug Dev. Ind. Pham. 26 (2000): 1077-1083.
6. G. P. Carino, J. S. Jacob, E. Mathiowitz, E, Nanosphere based oral insulin delivery. J. Controlled Release 65 (2000) 261-269.
7. F. Cilurzo, P. Minghetti, F. Selmin, A. Casiraghi, L. Montanari, Polymethacrylate salts as new lowswellable mucoadhesive materials. J. Controlled Release 88 (2003) 43-53.
8. S. S. Davis, Formulation strategies for absorption windows. Drug Disc. Today 10 (2005) 249-257.
9. G. Di Colo, S. Falchi, Y. Zambito, In vitro evaluation of a system for pH-controlled peroral delivery of metformin. J. Controlled Release 80 (2002) 119-128.
10. T. P. J. Dormans, J. J. M. vanMeyel, P. G. G. Gerlag, Y. Tan, F. G. M. Russel, P. Smits, Diuretic efficacy of high dose furosemidc in severe heart failure: Bolus injection versus continuous infusion. J. Am. College Cardio. 28 (1996) 376-382.
11. I. Gimenez, Molecular mechanisms and regulation of furosemide-sensitive Na—K—Cl cotransporters. Curr. Op. Nephrology Hypertension 15 (2006): 517-523.
12. M. M. Hammarlund, B. Odlind, L. K. Paalzow, Acute Tolerance to Furosemide Diuresis in Humans—Pharmacokinetic-Pharmacodynamic Modeling. *J. Pharm. And Exp. Thera.* 233 (1985) 447-453.
13. M. S. Kislalioglu, M. A. Khan, C. Blount, R. W. Goettsch, S. Bolton, Physical Characterization and Dissolution Properties of Ibuprofen—Eudragit Coprecipitates. J. Pharm. Sci. 80 (1991) 799-804.
14. B. Laulicht, P. Cheifetz, A. Tripathi, E. Mathiowitz, Are in vivo gastric bioadhesive forces accurately reflected by in vitro experiments? J. Controlled Release 134 (2009)103-110.
15. R. I. Moustafine, T. V. Kabanova, V. A. Kemenova, G. Van den Mooter, Characteristics of interpolyelectrolyte complexes of Eudragit E100 with Eudragit L100. J. Controlled Release 103 (2005): 191-198.
16. M. D. Murray, K. M. Haag, P. K. Black, S. D. Hall, D. C. Brater, Variable furosemide absorption
17. N. Ozdemir, S. Ordu, Y. Ozkan, Studies of floating dosage forms of furosemide: In vitro and in vivo evaluations of bilayer tablet formulations. Drug Dev. Ind. Pharm. 26 (2000) 857-866.
18. M. Sakkinen, J. Marvola, H. Kanerva, K. Lindevall, A. Ahonen, M. Marvola, Are chitosan formulations mucoadhesive in the human small intestine? An evaluation based on gamma scintigraphy. Int. J. Pharm. 307 (2006) 285-291.
19. M. Sakkinen, T. Tuononen, H. Jurjenson, P. Veski, M. Marvola, Evaluation of microcrystalline chitosans for gastro-retentive drug delivery. Eur. J. Pharm. Sci. 19 (2003): 345-353. S34, Suppl. 1.
20. D. R. K. Salvador, N. R. Rey, G. C. Ramos, F. E. R. Punzalan, Continuous infusion versus bolus injection of loop diuretics in congestive heart failure. Cochrane Database of Systematic Reviews (2005).
21. G. Santus, C. Lazzarini, G. Bottoni, E. P. Sandefer, R. C. Page, W. J. Doll, U. Y. Ryo, G. A. Digenis, An in vitro in vivo investigation of oral bioadhesive controlled release furosemide formulations.
Eur. J. Pharm. Biopharm. 44 (1997) 39-52.
22. S. C. Shin, I. J. Oh, Y. B. Lee, H. K. Choi, J. S. Choi, Enhanced dissolution of furosemide by coprecipitating or cogrinding with crospovidone. Int. J. Pharm. 175 (1998) 17-24.
23. N. Sistovaris, Y. Hamachi, T. Kuriki, Multifunctional Substances—Determination of pKA Values by Various Methods. Fresinius J. Analytical Chem. 340 (1991) 345-349.
24. T. Terao, K. Matsuda, H. Shouji, Improvement in site-specific intestinal absorption of furosemide by Eudragit L100-55. J. Pharm. Pharma. 53 (2001) 433-440.
25. K. Thoma, R. Klimek, Photostabilization of Drugs in Forms without Protection from Packaging Materials. Int. J. Pharm. 67 (1991) 169-175.
26. J. G. Vanderwatt, M. M. Devilliers, The Effect of Mixing Variables on the Dissolution Properties of Direct Compression Formulations of Furosemide. Drug Dev. Ind. Pharm. 18 (1995) 2047-2056.

What is claimed is:

1. A pharmaceutical composition formulation of a hydrophobic agent which is a loop diuretic, the formulation comprising a mixture of: the agent in a particulate form, and the agent in a phase inverted micronized form produced by phase inversion of a solution of the particulate form using a hydrophobic non-solvent, the phase inverted micronized form of the agent having increased hydrophobic molecular organization, and exhibiting increased hydrophobicity and delayed dissolution in water as compared to a micronized form produced by phase inversion without using the hydrophobic non-solvent.

2. The pharmaceutical composition according to claim 1, wherein the loop diuretic is selected from the group of: furosemide, azosemide, bumetanide, piretanide, torasemide, ethacrynic acid, etozolin, and a combination thereof.

3. The pharmaceutical composition according to claim 1, wherein the loop diuretic comprises furosemide.

4. A pharmaceutical composition formulation of a hydrophobic agent which is a loop diuretic, the formulation comprising a mixture of the agent in a particulate form and the agent in a phase inverted micronized form, wherein the size of the loop diuretic in phase inverted micronized form has a length range selected from: about 0.25 μm to about 5 μm; about 1 μm to about 4 μm; about 1 μm to about 5 μm; about 2 μm to about 3 μm;
about 2 μm to about 4 μm; about 2 μm to about 6 μm; about 3 μm to about 5 μm; and, about 3 μm to about 6 μm.

5. The pharmaceutical composition according to claim 1, further comprising a pharmaceutically acceptable salt or buffer.

6. The pharmaceutical composition according to claim 4, formulated as a unit dosage.

7. The pharmaceutical composition according to claim 6, wherein the dosage per weight of subject is selected from: about 0.05 mg/kg, about 0.1 mg/kg, about 1 mg/kg, about 2 mg/kg, about 5 mg/kg, or about 10 mg/kg.

8. A method for regulating diuresis in a subject afflicted with an edematous condition or disorder, the method comprising contacting the subject with an effective dosage of the composition according to claim 1.

9. The method according to claim 8, wherein regulating diuresis further comprises measuring urine output and observing greater bioavailability of the composition according to claim 1 than a non-micronized loop diuretic.

10. The method according to claim 8, wherein the edematous condition or disorder is selected from: congestive heart failure, cirrhosis, epidemic dropsy, nephrotic syndrome, chronic kidney disease, malnutrition, and thyroid disease.

11. The method according to claim 8, wherein the edematous condition or disorder comprises congestive heart failure.

12. The method according to claim 8, wherein regulating the diuresis further comprises measuring the rate of eliminating excess retained fluid from the subject and observing urine production as a consistent monotonic function of time in comparison to urine production resulting from treatment with a non-micronized loop diuretic.

13. The method according to claim 12, wherein the monotonic function comprises eliminating or reducing an initial diuretic spike of urine production in the subject and maintaining cumulative urine output.

14. The method according to claim 12, further comprising after the contacting the subject monitoring urine output.

15. The method according to claim 8, wherein the dosage per weight of subject treated is about 0.05 mg/kg, about 0.1 mg/kg, about 1 mg/kg, about 2 mg/kg, about 5 mg/kg, or about 10 mg/kg.

16. The pharmaceutical composition according to claim 4, wherein the loop diuretic is selected from the group of furosemide, azosemide, bumetanide, piretanide, torasemide, ethacrynic acid, etozolin, and a combination thereof.

17. The pharmaceutical composition according to claim 4, wherein the loop diuretic comprises furosemide.

18. The pharmaceutical composition according to claim 4, further comprising a pharmaceutically acceptable salt or buffer.

19. A method for regulating diuresis in a subject afflicted with an edematous condition or disorder, the method comprising contacting the subject with an effective dosage of the composition according to claim 4.

20. The method according to claim 19, wherein regulating diuresis further comprises measuring urine output and observing greater bioavailability of the composition than a non-micronized loop diuretic.

21. The method according to claim 19, wherein the edematous condition or disorder is selected from: congestive heart failure, cirrhosis, epidemic dropsy, nephrotic syndrome, chronic kidney disease, malnutrition, and thyroid disease.

22. The method according to claim 19, wherein the edematous condition or disorder comprises congestive heart failure.

23. The method according to claim 19, wherein regulating the diuresis further comprises measuring the rate of eliminating excess retained fluid from the subject and observing urine production as a consistent monotonic function of time in comparison to urine production resulting from treatment with a non-micronized loop diuretic.

24. The method according to claim 23, wherein the monotonic function comprises eliminating or reducing an initial diuretic spike of urine production in the subject and maintaining cumulative urine output.

25. The method according to claim 23, further comprising monitoring urine output after the contacting the subject.

26. The method according to claim 19, wherein the dosage per weight of subject treated is about 0.05 mg/kg, about 0.1 mg/kg, about 1 mg/kg, about 2 mg/kg, about 5 mg/kg, or about 10 mg/kg.

* * * * *